United States Patent
Heimburger et al.

(10) Patent No.: US 6,239,261 B1
(45) Date of Patent: May 29, 2001

(54) PASTEURIZED, PURIFIED VON WILLEBRAND FACTOR CONCENTRATE AND A PROCESS FOR THE PREPARATION THEREOF

(75) Inventors: Norbert Heimburger, Marburg; Gerhard Kumpe, Wetter; Klaus Wellner, Marburg, all of (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 08/253,232

(22) Filed: Jun. 2, 1994

Related U.S. Application Data

(63) Continuation of application No. 07/899,936, filed on Jun. 17, 1992, now abandoned, which is a continuation of application No. 07/759,983, filed on Sep. 16, 1991, now abandoned, which is a continuation of application No. 07/478,640, filed on Feb. 12, 1990, now abandoned.

(30) Foreign Application Priority Data

Feb. 14, 1989 (DE) ................................. 39 04 354

(51) Int. Cl.[7] ............................. C07K 1/00; C07K 1/36; A61K 38/37
(52) U.S. Cl. .................. 530/412; 530/380; 530/381; 530/382; 530/383; 530/418; 530/416; 530/419; 530/420
(58) Field of Search .................. 530/380, 381, 530/382, 383, 412, 416, 418, 419, 420

(56) References Cited

U.S. PATENT DOCUMENTS

| | | | | |
|---|---|---|---|---|
| 4,085,095 | * | 4/1978 | Bick et al. | 530/383 |
| 4,210,580 | | 7/1980 | Amrani . | |
| 4,272,523 | * | 6/1981 | Kotitschke | 530/382 |
| 4,543,210 | * | 9/1985 | Mitra et al. | 530/383 |
| 4,578,218 | | 3/1986 | Saundry et al. . | |
| 4,743,680 | * | 5/1988 | Mathews | 530/383 |
| 5,021,243 | * | 6/1991 | Becker et al. | 424/530 |

FOREIGN PATENT DOCUMENTS

| | | |
|---|---|---|
| 3504385A1 | 8/1985 | (DE) . |
| 0 022 052 | 1/1981 | (EP) . |
| 0 083 483 A1 | 7/1983 | (EP) . |
| 2 079 292 | 1/1982 | (GB) . |

OTHER PUBLICATIONS

"The Properties of Factor VIII Coagulant Activity Prepared by Immunoadsorbent Chromatography," J. Lab. Clin. Med., 93, 40 (1979).
"The Chromatographic Separation o f Factor VIII on Aminohexyl Sepharose," British Journal of Haematology, 43, 1979, pp. 669–674.
Harris et al "Protein Purfication Methods . . . " 57–64 1989.*
Scopes in "Protein Purification : Principles and Practice" Spriner Verlag, New York pp 43–52, (1982).*
Wang et al. (1988) J. Parenteral. Sci & Technology 42 Suppl 25, 53–526.*
Burnouf–Radosevich "Chromatographic Preparation of a Therapeutic Highly Purified von Willebrand Factor Concentrate from Human Hyoprecipitate" Vox Sang 62 1–11 1992.*
Baugh etal. "Separation of Human Factor VIII Activity from the von Willebrand's Antigen & Risoceteu Platelet Aggregating Activity" Biochim et Biophys Acta 371 370–367 1974.*

* cited by examiner

*Primary Examiner*—David Guzo
*Assistant Examiner*—Gerald G. Leffers, Jr.
(74) *Attorney, Agent, or Firm*—Finnegan, Henderson, Farabow, Garrett and Dunner, L.L.P.

(57) ABSTRACT

A process for the preparation of a concentrate of von Willebrand factor is described, entailing a solution of a complex of this factor with factor VIII:C being optionally pasteurized and treated with an anion exchanger, there being no binding of the von Willebrand factor.

16 Claims, No Drawings

PASTEURIZED, PURIFIED VON WILLEBRAND FACTOR CONCENTRATE AND A PROCESS FOR THE PREPARATION THEREOF

This application is a continuation of application Ser. No. 07/899,936, filed Jun. 17, 1992, now abandoned, which is a continuation of application Ser. No. 07/759,983, filed Sep. 16, 1991, abandoned, which is a continuation of application Ser. No. 07/478,640, filed Feb. 12, 1990, abandoned.

The invention relates to a process for the preparation of a purified and pasteurized von Willebrand factor concentrate, and to such a concentrate which has been prepared by this process and is suitable for the treatment of von Willebrand syndrome.

The latter syndrome is characterized by a congenital deficiency and/or defect of von Willebrand protein.

There is a need for a pure and virus-safe von Willebrand factor concentrate because increasingly better purified factor VIII:C concentrates, which now contain only traces of von Willebrand factor, are being used for the treatment of hemophilia A.

Since von Willebrand patients have to receive life-long therapy, with high doses in some cases, a product of great purity and safety is indicated. Advantageous preparations are low in fibrinogen, immunoglobulins and isoagglutinins.

In the plasma, von Willebrand factor circulates in a concentration of 5–10 mg/l and in the form of a non-covalently bonded complex with factor VIII, the so-called antihemophilic globulin. In cryoprecipitate, von Willebrand factor is greatly enriched as von Willebrand factor/factor VIII complex and can be isolated therefrom or from plasma or plasma fractions using known fractionation methods.

German Offenlegungsschrift 3,504,385 (U.S. Pat. No. 4,578,218) discloses a process for the treatment of factor VIII complex, in which a factor VIII preparation is bound to an insoluble matrix which carries free sulfate groups, for example dextran sulfate, but evidently no separation of factor VIII complex into factor VIII:C and von Willebrand factor is possible in this case.

GB 2,079,292 describes a process for obtaining a von Willebrand factor from cryoprecipitate, but this does not separate factor VIII:C from von Willebrand factor either.

EP 0,022,052 (U.S. Pat. No. 4,210,580) describes a process in which plasma is treated with sodium heparin, whereupon fibronectin precipitates out together with von Willebrand factor. Antihemophilic factor is obtained from the supernatant. The precipitate is chromatographed on DEAE-cellulose, and fibronectin is obtained. It is stated that when agarose gel is used for the chromatography von Willebrand factor is eluted in the void volume. However, the amounts of heparin used are costly and gel filtration is a bottleneck for preparation on the industrial scale. In addition, toxic KSCN is used.

In European Patent 0,083,483 it is stated, on the state of the art, that J.Lab.Clin.Med. 93, 40 (1979) describes a process for separating factor VIII:C and von Willebrand factor, where the separation is brought about by immunoadsorption. However, only the factor VIII:C is obtained in sufficient purity in this process.

Another process for separating these two factors is described in Brit.J.Haematol. 43, 669 (1979), with aminohexyl-agarose being used. This process is also unsuitable for obtaining von Willebrand factor.

EP 0,083,483 itself describes a process for obtaining factor VIII:C which contains only small amounts of von Willebrand factor. However, no process for obtaining von Willebrand factor is described therein.

It is common to all these processes that they do not lead to complete dissociation of the complex with subsequent quantitative liberation of a native F VIII:C and vWF. None of these processes describes a pasteurized, and thus virus-safe, product. In order to protect the vWP from proteolytic decomposition during the purification, toxic substances such as DFP and soybean trypsin inhibitor or else buffers such as KSCN and $NaN_3$ are used in these processes. Finally, these processes have disadvantages because they contain steps which represent a bottleneck for large-scale manufacture. These include, for example, gel filtrations, i.e. separation according to molecular weight or chromatographic steps using a salt gradient for the elution.

The present invention describes a process with which it is possible, surprisingly, to dissociate the complex of factor VIII:C and von Willebrand factor and to isolate von Willebrand factor purified and pasteurized in high yield. The object of this invention is to obtain a purified, pasteurized, and thus virus-safe, coagulating therapeutic agent for the treatment of von Willebrand syndrome.

The invention relates to a process for the preparation of a pasteurized von Willebrand factor concentrate, which comprises a solution which contains von Willebrand factor (vWF) as complex with F VIII:C in a buffer of pH 5.5 to 6.5, which contains amino acids and has a carbohydrate concentration of 5–30% w/w, being treated with an anion exchanger to which F VIII:C binds, and the von Willebrand factor concentrate being obtained from the solution.

It is possible to use as starting material for the preparation of a vWF concentrate solutions in which the vWF is present as complex with F VIII:C, for example plasma and fractions obtained therefrom, such as cryoprecipitate, Cohn fraction I or else supernatants and extracts from cell cultures.

The starting material, preferably cryoprecipitate or an intermediate fraction obtained therefrom, can have been pasteurized.

The vWF can be protected from thermal inactivation during the pasteurization by the addition of carbohydrates, preferably sucrose, preferably in concentrations of 10–60% (w/w), and/or amino acids, preferably glycine, preferably in concentrations of 0.5–3.0 mol/l, and/or calcium salts, preferably 1–20 mmol/l. It is also possible by these measures simultaneously to prevent the precipitation of acid-sensitive proteins, for example of fibronectin.

The carbohydrates act not only to protect the proteins from thermal inactivation or denaturation, but also as solubilizers in the acidic pH range from 6.5 to 5.5, particularly for fibrinogen and vWF in this context, in that they surprisingly prevent precipitation.

After an adsorption of the F VIII:C onto the ion exchanger, the vWF can be kept in solution at pH 5.5, and from this the fibrinogen can be removed by addition of glycine in concentrations of 0.5–3 mol/l, preferably 2.7 mol/l, and the vWF can be precipitated from the glycine supernatant with NaCl concentrations corresponding to 2–15% (v/v), preferably 6% (w/v).

The prepurified vWF intermediate product can be pasteurized a second time to increase the virus safety.

The pasteurized and highly purified vWF can be sterilized by filtration and lyophilized, for example with glycine (2% w/v), albumin (0.5%) in citrated (0.02 mol/l) NaCl (0.06 mol/l) as stabilizers.

The conditions for the dissociation and purification can be transferred to large-scale manufacture.

In contrast to antihemophilic cryoprecipitate, crude cryoprecipitate or cryofractions which have hitherto been used for the treatment of vW syndrome, the product according to the invention is virtually free of ballast proteins.

The process according to the invention complies with the stringent requirements relating to purity, yield and virus safety: viruses which are possibly present are eliminated, together with the ballast proteins, by the purification process, and are inactivated by a pasteurization. The specific activity of a product prepared by the described process is above 100 U of F VIIIR:CoF/mg of protein.

The procedure can be as follows:

Dissolved cryoprecipitate which is greatly enriched in von Willebrand factor and factor VIII and from which the factors of the prothrombin complex have been removed by an $Al(OH)_3$ adsorption is stabilized in a manner known per se by addition of carbohydrates, amino acids and calcium ions to protect against thermal inactivation and is heated in aqueous solution at 60° C., preferably for 10 h.

The pasteurized solution can be diluted with a buffer of physiological conductivity (12–15 mS) and a pH of 5.5 and the composition 0.2 mol/l lysine and 0.2 mol/l sodium acetate to twice the volume, the pH of the solution adjusted to 5.5 and an anion exchanger added at 20° C.

Under these conditions, the factor VIII binds to basic ion exchangers with DRAK and QAR as functional groups bonded to "SEPHADEX", "SEPHAROSE", cellulose or "FRACTOGEL" as matrix, whereas vWz remains in solution. These exchangers are previously equilibrated with the following buffer for this purpose: 0.1 mol/l sodium acetate, 0.1 mol/l lysine, 0.017 mol/l NaCl, pH 5.5.

Since, under the stated conditions, vWF remains together with fibrinogen and fibronectin in the supernatant, it is evident that under the stated conditions the complex of vWF with factor VIII is dissociated.

The anion exchanger loaded with P VIII can be washed with buffer solution containing 0.1 mol/l lysine, 0.1 mol/l sodium acetate, 0.017 mol/l NaCl, pH 5.5, or other buffers with a conductivity of 12–15 mS. Used for the elution are buffers with a high salt concentration, for example 0.3–1 mol/l NaCl or other alkali metal or alkaline earth metal halides.

The eluate can, where appropriate, be worked up to give a pasteurized and highly purified F VIII:C concentrate.

The described dissociation and selective adsorption in the acid pH range is possible only when the fibrinogen, which represents the major amount of protein in the solution, does not precipitate out, because it is known that euglobulins, of which fibrinogen is one, are precipitated out in aqueous solution by acidification to pH 5 to 5.5.

This does not apply to the process according to the invention, because the carbohydrates remaining in the solution from the pasteurization, and the calcium, keep the fibrinogen in solution even at an acid pH.

This process step likewise forms part of the subject-matter of the present invention, even though the pasteurization of the proteins takes place at a later time.

The von Willebrand factor which is free of factor VIII:C activity remains together with the fibrinogen and the fibronectin in the supernatant (batch process) or passes through the column and can subsequently be separated by suitable fractionation steps from the concomitant proteins which are present in large excess in terms of amount, for example by a glycine fractionation and NaCl precipitation of the anion exchanger supernatant.

For this purpose, the DEAE supernatant is adjusted to pH 7.3, and the fibrinogen is precipitated with 0.5–3 mol/l glycine, preferably with 2.7 mol/l, at 37° C. and is removed.

The von Willebrand factor is selectively precipitated out by addition of solid or dissolved NaCl to the glycine supernatant to a final concentration of 2–15% w/v, preferably 6% w/v, and is removed, for example in a centrifuge.

The dissolved precipitate can be purified even further by treatment with "$^R$AEROSIL", powders made by condensing silica from the vapor phase at elevated temperature and also referred to as pyrogenic silica. Concomitant proteins of vWF, namely fibrinogen, fibronectin and immunoglobulins, are preferentially bound by the AEROSIL at a particular protein concentration which is adjusted via the OD at 280 nm; the undesired isoagglutinins are also distinctly reduced. The AEROSIL treatment can take place both before and after the pasteurization.

The von Willebrand factor precipitate which has been prepared in this way can be dissolved, mixed with sucrose/glycine and, in order to increase the virus safety, again heated at 60° C. for 10 h. This pasteurization is, surprisingly, possible virtually without loss of activity. The residual fibrinogen which is still present is precipitated out of the cooled and diluted solution by a glycine precipitation with 0.5–3.0 mol/l, preferably 2.2 mol/l. The von Willebrand factor can be isolated in highly pure form, and with a low isoagglutinin titer, by a subsequent sodium chloride precipitation of the supernatant with 2–15% w/v, preferably 8% w/v.

After the von Willebrand factor has been dissolved in a buffer composed of 0.02 mol/l citrate, 0.06 mol/l NaCl, pH 6.8, and stabilized by addition of amino acids and albumin, dialysis is subsequently carried out; the product is then sterilized by filtration and, where appropriate, lyophilized. The enrichment of vWF was determined via the F VIIIR:CoF activity by the agglutination method.

Stabilized platelets are agglutinated in the presence of F VIIIR:CoF and the antibiotic ristocetin A.

Determination procedure:

50 µl of von Willebrand reagent, Behringwerke (resuspended in 1 ml of distilled water) and 50 µl of plasma or plasma dilution are mixed on a glass plate and swirled at room temperature for one minute, either on a shaker or by hand; care must be taken that the sample is well mixed. After one minute has elapsed, the degree of agglutination is compared with a sodium chloride control. The dilution level which is still positive by comparison with the sodium chloride control is read off and multiplied by the sensitivity of the reagent. The P VIIIR:CoF content in percent is obtained.

The examples which follow describe the preparation of a pasteurized, highly purified von Willebrand factor concentrate.

EXAMPLE 1

1. Starting material 1 kg of crude cryoprecipitate was dissolved, by heating at 30–37° C., in 3 l of a buffer which contained 0.08 mol/l NaCl, 0.27 mol/l glycine, 0.13 U/ml antithrombin III and 0.66 USP U/ml heparin. The result was 4 l of solution with a pH of 6.8–6.9 and the following additives in the following concentrations

| NaCl | 0.06 mol/l |
|---|---|
| glycine | 0.2 mol/l |
| AT III | 0.1 U/ml |
| heparin | 0.5 U/ml. |

2. $Al(OH)_3$ adsorption 80 ml of a 1% strength $Al(OH)_3$ suspension (Behringwerke, Marburg) were added to 1000 ml of solution from 1 and stirred for 15 min, temperature: 28–30° C. It was then centrifuged at 3000×g for 15 min, the residue was discarded, and the supernatant was mixed with stabilizers and pasteurized.

3. Stabilization and pasteurization 1000 ml of supernatant from 2 were mixed with the following stabilizers:

5 ml of CaCl$_2$ solution, 1 mol/l (5 mmol/l)

1000 g of sucrose (500 g/kg of solution)

150 g of glycine (2 mol per 1 l of solution).

The pH was adjusted to 7.3 with 2 N NaOH. The volume of the solution was increased by the additions. Starting from 1 kg of cryoprecipitate, 6.8 l of stabilized solution were obtained, and this was heated in a waterbath at 60° C. for 10 h.

4. Ion exchanger treatment 6.8 l of solution from 3 were diluted with 6.8 l of a buffer which contained 0.2 mol/l sodium acetate, pH 5.5 and 0.2 mol/l lysine. The pH was adjusted to 5.5 with dilute acetic acid.

The solution was mixed with 300 ml of DEAE-$^R$Sepharose CL 6B which had been equilibrated with a buffer of pH 5.5 which contained 0.1 mol/l sodium acetate, 0.1 mol/l lysine, 1 g/l NaCl. The suspension was stirred at room temperature for 2–3 hours, and the progress of the adsorption was monitored by continuous F VIII determinations. The loaded resin was then poured onto a nylon filter bag and separated off, washed, eluted, and the eluate was worked up to P VIII:C concentrate.

Obtaining the von Willebrand factor from the DEAE supernatant.

5. 2.7 M glycine precipitation

For the precipitation, the DRAE supernatant was adjusted to pH 6.8 with 2 M NaOH, heated to 37° C. and adjusted by addition of 2.1 mol/l crystalline glycine (157.5 g) to a final concentration of 2.7 mol/l, since the DEAE supernatant already contains 0.6 mol/l glycine from the pasteurized solution. The glycine was metered in slowly over 30 min, while stirring. During this the fibrinogen precipitates and is separated out. The precipitation mixture cools to 20–25° C. during this. The fibrinogen precipitate is removed by centrifugation at 3000–5000×g.

6. 6% NaCl precipitation

The von Willebrand factor was precipitated by addition of crystalline NaCl to the 2.7 molar glycine supernatant (60 g/l). The precipitation was carried out at room temperature; the NaCl was metered in over 30 min and the mixture was then stirred for 30 min. The fine precipitate was removed in a continuous flow centrifuge at 15,000×g and 10° C. with a throughput of 40 l/h.

7. Dissolution of the 6% NaCl residue, stabilization and pasteurization

The 6% NaCl residue was dissolved in 60 ml of distilled water. 82.5 ml of a solution with an optical density of 40 at 280 nm were obtained. If the optical density is greater than 50 the mixture is diluted to this value.

For stabilization, 82.5 g of sucrose (1 g/ml) and 12.3 g of glycine (2 mol/l) were added to 82.5 ml of solution. The volume of the stabilized solution was 140 ml, the pH was adjusted to 6.8 with 2 M NaOH, and the stabilized solution was heated at 60° C. for 10 h.

8. Isolation of the pasteurized von Willebrand factor from the stabilizer solution Dilution:

The pasteurized solution was cooled to 40° C. and then diluted in the ratio 1:3 with 280 ml of a buffer which contained 0.03 mol/l NaCl and 0.02 mol/l trisodium citrate. The optical density of the solution at 280 nm was 7.81 after dilution.

Preliminary glycine precipitation (2.2 mol/l)

56.7 g of glycine (1.8 mol/l) were added to 420 ml of the diluted and pasteurized solution, which already contained 0.4 mol/l glycine, at 35° C. The solution cooled during the precipitation (30 min) and the subsequent stirring time (30 min) to 25° C.

The precipitate was removed by centrifugation at 3000 g and discarded.

8% NaCl precipitation 0.38 times the volume of a precipitating medium (159.6 ml) which contained 1.8 mol of glycine and 300 g of NaCl per liter was added to the 2.2 molar glycine supernatant (420 ml). The temperature during the precipitation was 20° C., and the precipitation and stirring time totalled 1 hour. The 8% NaCl residue which contained von Willebrand factor HS was removed by centrifugation at 5000 g.

Dissolution of the 8% NaCl residue, dialysis, ultracentrifugation:

The 8% NaCl residue was dissolved in 33 ml of a dissolving buffer of pH 6.9 and the following composition:

| Dissolving buffer: | 0.06 mol/l | NaCl |
|---|---|---|
| | 0.02 mol/l | trisodium citrate |
| | 2% | glycine |
| | 0.5% | human albumin. |

The solution was dialyzed against 1.2 l of a dialysis buffer, stirring at 20° C. for 2×1.5 h:

| Dialysis buffer: | 0.06 mol/l | NaCl |
|---|---|---|
| | 0.02 mol/l | trisodium citrate |
| | 2% | glycine |
| | (pH 6.8–6.9). | |

The dialysate (69 ml) was adjusted with human albumin to a final concentration of 0.5% and centrifuged at 15,000 g and 20° C. for 60 min until clear.

For the sterilization by filtration, the ultracentrifuged solution was made up to 110 ml with dissolving buffer.

Sterilization by filtration, adjustment of concentration, packaging and lyophilization:

The ultracentrifuged solution of the von Willebrand factor HS concentrate (110 ml) was heated to 30–35° C. and then sterilized by filtration through a plate filter of pore widths 0.45 $\mu$m and 0.2 $\mu$m. The solution contained 160 U/ml F VIIIR:CoF activity.

EXAMPLE 2

As in Example 1, paragraph 6, a 6% NaCl precipitate was obtained, and the von Willebrand factor was purified further by treatment with AEROSIL. For this, the precipitate was first dissolved in 60 ml of distilled water, the optical density (OD) at 280 nm was measured, and the solution was then diluted to 200 ml with an OD of 10. Moist AEROSIL 200 was added to this solution (5 mg/ml based on dry substance), and the suspension was stirred at 20° C. for 30 min; the AEROSIL, which was loaded with von Willebrand factor concomitant proteins, was then removed by centrifugation, and the supernatant was worked up to the final product as described in detail in Example 1. This product had a specific activity which was higher by a factor of 2 to 4, while the high yield was unchanged.

What is claimed is:

1. A process for the preparation of a and purified von Willebrand factor concentrate, which comprises:

a) preparing a solution selected from the group consisting of cryoprecipitate, Cohn fraction I, a supernatant of a cell culture and an extract of a cell culture, said solution having a pH of 5.5 to 7.3, and containing von Willebrand factor (vWp) as a complex with F VIII:C, a carbohydrate at a concentration of 5–30% w/w, calcium ion, and amino acids;

b) treating said solution with an anion exchanger to which F VIII:C binds to obtain a von Willebrand factor concentrate free of F VIII:C;

c) treating the von Willebrand factor solution free of F VIII:C with 0.5 to 3 mol/l glycine to precipitate proteins from said solution;

d) removing the protein precipitate from said solution to form a glycine supernatant solution containing von Willebrand factor;

e) adding NaCl at a concentration of 2–15% w/v to said glycine supernatant solution to precipitate von Willebrand factor; and f) recovering precipitated von Willebrand factor.

2. The process as claimed in claim 1, wherein the concentration of glycine is 2.7 mol/l.

3. The process as claimed in claim 1, wherein the concentration of NaCl is 6% (w/v).

4. The process as claimed in claim 1, wherein the carbohydrate is sucrose.

5. The process as claimed in claim 1, wherein the solution containing von Willebrand factor as a complex with F VIII:C has a pH of 5.5 to 6.5.

6. The process as claimed in claim 1, wherein a solution of the recovered von Willebrand factor is treated with pyrogenic silica.

7. A process as claimed in claim 1, wherein a solution of the recovered von Willebrand factor is pasteurized.

8. A process as claimed in claim 1, wherein a solution of the recovered von Willebrand factor is pasteurized and treated with pyrogenic silica.

9. The process as claimed in claim 1, wherein the cryoprecipitate solution which contains von Willebrand factor is a pasteurized cryoprecipitate solution.

10. The process as claimed in claim 1, wherein the recovered von Willebrand factor is treated in solution with pyrogenic silica.

11. The process as claimed in claim 1, wherein the recovered von Willebrand factor precipitate is pasteurized in solution and treated in solution with pyrogenic silica.

12. The process as claimed in claim 1, further comprising adding 2% (w/v) glycine, 0.5% albumin, 0.02 mol/l citrate and 0.06 mol/l NaCl to the and purified von Willebrand factor to form a solution of von Willebrand factor, sterilizing the solution of von Willebrand factor by filtration and lyophilizing the filtered solution containing sterilized von Willebrand factor.

13. The process as claimed in claim 1, wherein a solution of the recovered von Willebrand factor is pasteurized and protected from thermal inactivation during pasteurization by the addition of sucrose in a concentration of 10–60% w/v, glycine in a concentration of 0.5–3.0 mol/l, and a calcium salt in a concentration of 1–20 mmol/l, and the precipitation of acid-sensitive proteins is simultaneously prevented thereby.

14. The process as claimed in claim 13, wherein pasteurization is carried out by heating at 60° C. for 10 hours.

15. The process as claimed in claim 6, wherein the acid-sensitive proteins are fibrinogen and fibronectin.

16. The process as claimed in claim 13, wherein the recovered von Willebrand factor is treated in solution with pyrogenic silica.

* * * * *

UNITED STATES PATENT AND TRADEMARK OFFICE
CERTIFICATE OF CORRECTION

PATENT NO. : 6,239,261 B1 Page 1 of 1
DATED : May 29, 2001
INVENTOR(S) : Norbert Heimburger et al.

It is certified that error appears in the above-identified patent and that said Letters Patent is hereby corrected as shown below:

Column 6,
Line 66, before "purified", delete "and".

Column 7,
Line 5, "(vWp)" should read -- (vWF) --.

Column 8,
Line 14, before "purified", delete "and".
Line 29, "claim 6" should read -- claim 13 --.

Signed and Sealed this

Twenty-second Day of October, 2002

Attest:

JAMES E. ROGAN
Attesting Officer    Director of the United States Patent and Trademark Office